United States Patent
McEwen et al.

(10) Patent No.: US 8,721,678 B2
(45) Date of Patent: May 13, 2014

(54) SURGICAL TOURNIQUET CUFF SYSTEM

(75) Inventors: James A. McEwen, Vancouver (CA); Michael Jameson, North Vancouver (CA)

(73) Assignee: Western Clinical Engineering Ltd., Vancouver, CA (US)

( * ) Notice: Subject to any disclaimer, the term of this patent is extended or adjusted under 35 U.S.C. 154(b) by 933 days.

(21) Appl. No.: 12/401,206

(22) Filed: Mar. 10, 2009

(65) Prior Publication Data

US 2009/0171223 A1    Jul. 2, 2009

Related U.S. Application Data

(63) Continuation of application No. 11/219,016, filed on Sep. 1, 2005, now abandoned, which is a continuation-in-part of application No. 11/198,565, filed on Aug. 5, 2005, now Pat. No. 7,955,352.

(51) Int. Cl.
*A61B 17/12* (2006.01)
*A61B 17/135* (2006.01)
*A61B 5/11* (2006.01)

(52) U.S. Cl.
USPC ........................................... 606/203; 606/202

(58) Field of Classification Search
USPC .................. 606/202–203; 604/163, 171, 263; 340/539.12; 73/40, 49.2, 46, 700, 756; 128/204.18–204.22; 600/485–486, 600/494, 561
See application file for complete search history.

(56) References Cited

U.S. PATENT DOCUMENTS

| | | | |
|---|---|---|---|
| 4,877,033 A | 10/1989 | Seitz, Jr. | |
| 5,181,522 A * | 1/1993 | McEwen | ........................ 600/561 |
| 5,411,518 A | 5/1995 | Goldstein et al. | |
| 5,433,221 A * | 7/1995 | Adair | ............................ 128/849 |
| 5,651,368 A | 7/1997 | Napolitano et al. | |
| 5,669,390 A * | 9/1997 | McCormick et al. | ......... 600/499 |
| 5,931,853 A * | 8/1999 | McEwen et al. | ............... 606/203 |
| 6,117,086 A * | 9/2000 | Shulze | .......................... 600/488 |
| 6,213,939 B1 * | 4/2001 | McEwen | ........................ 600/202 |
| 6,682,547 B2 | 1/2004 | McEwen et al. | |
| 7,166,123 B2 * | 1/2007 | Hovanes et al. | ............... 606/202 |
| 2002/0099297 A1 | 7/2002 | Nakagawa et al. | |
| 2002/0107461 A1 * | 8/2002 | Hui | ............................... 601/149 |
| 2003/0036771 A1 * | 2/2003 | McEwen et al. | ............... 606/202 |
| 2004/0003814 A1 * | 1/2004 | Banner et al. | ............. 128/204.21 |
| 2004/0127937 A1 * | 7/2004 | Newton | .......................... 606/202 |
| 2004/0186355 A1 | 9/2004 | Strong et al. | |
| 2006/0122517 A1 * | 6/2006 | Banet et al. | ................... 600/485 |

OTHER PUBLICATIONS

Supplementary EP Search Report for EP App claiming a common priority app. 4 pages; Apr. 11, 2012.

* cited by examiner

*Primary Examiner* — Mark Mashack
(74) *Attorney, Agent, or Firm* — Hancock Hughey LLP (57) ABSTRACT

A surgical tourniquet cuff system includes a tourniquet cuff with a cuff connector for communicating pneumatically with the cuff and for releasably connecting to a tourniquet instrument connector to establish a pneumatic passageway between the cuff connector and the tourniquet instrument connector. A tourniquet instrument supplies pressurized gas through the pneumatic passageway to the cuff. The tourniquet instrument connector includes a cuff pressure transducer for producing a cuff pressure signal indicative of the pressure of gas within the gas passageway near the connection. The cuff may include a cuff usage register for containing a cuff usage record and the tourniquet instrument connector may include a cuff usage register interface for reading the record. The tourniquet cuff may further include a cuff sheath forming a flexible conduit containing the cuff connector and sized to allow the connection of the cuff connector to the tourniquet instrument connector within the sheath.

13 Claims, 7 Drawing Sheets

SURGICAL TOURNIQUET CUFF SYSTEM

FIELD OF THE INVENTION

This invention pertains to pneumatic tourniquet cuffs commonly used for stopping arterial blood flow into a portion of a surgical patient's limb to facilitate the performance of a surgical procedure, and for facilitating intravenous regional anesthesia.

BACKGROUND

A typical surgical tourniquet system of the prior art includes an inflatable tourniquet cuff for encircling a patient's limb at a desired location and a tourniquet instrument for supplying the tourniquet cuff with gas at a pressure sufficient to stop the flow of arterial blood past the cuff and into the limb. The tourniquet cuff typically includes an inflatable portion communicating pneumatically through a cuff port with a cuff connector that is releasably attachable to the tourniquet instrument through an instrument connector and flexible instrument tubing. This releasable connection establishes a pneumatic passageway for pressurized gas to pass between the tourniquet instrument and the inflatable portion of the cuff.

Many types of surgical tourniquet systems, including tourniquet cuffs and tourniquet instruments, have been described in the prior art, such as those described by McEwen in U.S. Pat. No. 4,469,099, U.S. Pat. No. 4,479,494, U.S. Pat. No. 5,439,477 and by McEwen and Jameson in U.S. Pat. No. 5,556,415 and U.S. Pat. No. 5,855,589. Many prior-art tourniquet instruments include a pressure regulator to increase and decrease the pressure of gas in the pneumatic passageway at the instrument end of the passageway to maintain the pressure in the inflatable portion of the cuff near a reference pressure that is above a minimum pressure required to stop arterial blood flow past the cuff during a time period suitably long for the performance of a surgical procedure. Some tourniquet instruments of the prior art, as described for example by McEwen in U.S. Pat. No. 4,469,099, include audio-visual alarms to promptly alert users to any significant over-pressurization or under-pressurization of a connected tourniquet cuff away from a selected tourniquet reference pressure, and include audio-visual alarms to alert users to any excessive periods of pressurization of a connected cuff, because the surgical literature clearly shows that such conditions are hazardous and are associated with increased probabilities of tourniquet-related injuries to patients. A few tourniquet systems of the prior art, such as those described by McEwen in U.S. Pat. No. 4,479,494 and U.S. Pat. No. 5,439,477, include physiologic transducers to help automatically determine the minimum and safest tourniquet reference pressure required to stop arterial blood flow in the limbs of individual patients undergoing specific surgical procedures.

In many tourniquet systems of the prior art, a pressure transducer located within tourniquet instrument is employed to sense the pressure of gas at the instrument end of the pneumatic passageway between the instrument and the tourniquet cuff, and that pressure is displayed for surgical staff as an estimate of the actual tourniquet cuff pressure and is employed by the pressure regulator of the tourniquet instrument. In such systems, the pressure transducer senses cuff pressure indirectly and remotely from the tourniquet cuff through long and flexible instrument tubing and an instrument connector. Accordingly, the accuracy of the estimated cuff pressure may be affected by partial or complete obstructions of the pneumatic passageway within the tourniquet instrument, instrument tubing, instrument connector and within the tourniquet cuff.

In prior-art tourniquet systems where cuff pressure is estimated remotely by a pressure transducer located within the tourniquet instrument, a variety of hazards may arise. For example, a complete obstruction may allow the actual pressure in the inflatable portion of the cuff to decrease substantially below the desired tourniquet pressure to a level where the cuff may be completely depressurized, or to increase substantially above the desired tourniquet pressure, without any indication to the surgical staff. In effect, the monitoring and regulation of cuff pressure may stop at the location of the obstruction. Also, any complete obstruction may render ineffective any audio-visual safety alarms of a connected prior-art tourniquet instrument intended to warn of hazardous over-pressurization or under-pressurization of the cuff, such as the safety alarms described by McEwen in U.S. Pat. No. 4,469,099. As another example, a partial obstruction may increase the pneumatic flow resistance at the location of the partial obstruction, and thus may reduce the ability of a connected tourniquet instrument to accurately and rapidly indicate changes in the actual cuff pressure and to rapidly and accurately regulate cuff pressure. Also, prior-art tourniquet systems in which cuff pressure is estimated remotely by a pressure transducer located within the tourniquet instrument may not be capable of detecting and responding rapidly, safely and appropriately to interruptions and large leaks caused by unanticipated malfunctions or failures of any of the pneumatic components forming the pneumatic passageway.

To improve safety and performance, some tourniquet systems of the prior art, often called dual-port tourniquet systems, establish two separate pneumatic passageways between the tourniquet instrument and the inflatable portion of the cuff. In one dual-port tourniquet system of the prior art, described in U.S. Pat. No. 4,469,099, the pneumatic pressure regulation elements within the tourniquet instrument communicate with the inflatable portion of the tourniquet cuff through one pneumatic passageway, and a pressure transducer within the tourniquet instrument communicates pneumatically with the inflatable portion of the cuff through a separate pneumatic passageway. Under normal operating conditions, this provides surgical staff with a more accurate indication of cuff pressure and enables the tourniquet instrument to increase the accuracy and speed of cuff pressure regulation. However, such dual-port tourniquet systems still sense cuff pressure by means of a pressure transducer located within the tourniquet instrument and thus their accuracy, performance and safety may be affected by flow resistances, partial obstructions, complete obstructions, interruptions and large leaks within their dual pneumatic passageways.

Tourniquet cuffs of the prior art can be grouped into three broad categories by their intended usage: (1) reusable tourniquet cuffs manufactured for usage outside the sterile surgical field in multiple surgical procedures, and for cleaning by users between successive procedures; (2) reusable tourniquet cuffs manufactured for usage within the sterile surgical field in multiple surgical procedures, and for cleaning and sterilization by specified sterilization processes between successive procedures; and (3) disposable tourniquet cuffs manufactured as sterile products suitable for usage within the sterile surgical field in one surgical procedure, and for disposal after the procedure.

Tourniquet cuffs of the prior art manufactured for use as sterile products within the sterile surgical field typically have long ports between the cuff connectors and the inflatable portions of such cuffs, allowing such cuffs to be applied and used within the sterile surgical field and to be connected to non-sterile tourniquet instrument connectors and non-sterile instrument tubing outside the sterile field. However, such long ports may interfere with the application of the cuff to the limb or may inadvertently make contact outside of the sterile field during cuff application and may thus contaminate the sterile cuff or surgical personnel. For certain surgical procedures, the desired sterile field may be very large and even very long ports of arbitrary lengths determined by the manufacturer may not be sufficiently long to extend beyond the desired sterile field. Also, including long ports in prior-art cuffs intended for use in a sterile surgical field adds to their cost of manufacture, an important consideration if the cuff is intended for disposal after a single surgical procedure. Also, increasing the lengths of the ports of sterile cuffs and sterilizable cuffs of the prior art to allow their connection to non-sterile instrument connectors and instrument tubing may increase pneumatic flow resistance, may affect the accuracy of cuff pressure indication and regulation, and may increase the likelihood of partial or complete occlusions of the pneumatic passageway, as described above.

In U.S. patent application Ser. No. 11/153,667 McEwen et al. describe a tourniquet cuff that has minimal flow restrictions within the pneumatic passageway of the cuff under normal operating conditions, that has a substantially reduced likelihood of partial or complete obstructions or interruptions of the pneumatic passageway within the cuff under foreseeable operating conditions, that can indicate exposure of the cuff to one or more external agents that are capable of affecting the integrity of the pneumatic passageway of the cuff before use, and that can be manufactured economically. However, McEwen et al. Ser. No. 11/153,667 does not address hazards that may arise due to flow restrictions and partial or complete obstructions of the portion of the pneumatic passageway external to the tourniquet cuff that are within the tourniquet instrument, the instrument tubing and the instrument connector.

In U.S. Pat. No. 6,682,547 McEwen et al. describe a tourniquet cuff having identification means indicative of a physical characteristic of the cuff and detectable by a connected tourniquet instrument. In U.S. Pat. App. Pub. US 20030167070 A1, McEwen et al. describe an adaptive tourniquet cuff system in which a tourniquet cuff carries identification means indicative of a physical characteristic of the cuff and in which a connected tourniquet instrument may automatically detect the physical characteristic of the cuff and adapt its operation in response to the detected physical characteristic. McEwen US 20030167070 A1 also describes the identification by a tourniquet instrument of prior exposure of a connected cuff to a potentially hazardous re-sterilization process. In U.S. patent application Ser. No. 11/153,667 McEwen et al. describe a disposable tourniquet cuff having means visually detectable by a user and automatically detectable by a connected tourniquet instrument to indicate exposure of the cuff to re-sterilization processes, indicating re-sterilization and possible reuse of a cuff originally manufactured and supplied as a sterile, single-use product. However, McEwen et al. '547, McEwen et al. US 20030167070 A1 and McEwen et al. Ser. No. 11/153,667 do not describe means for limiting the usage of a specific tourniquet cuff so that its usage does not exceed a safe usage limit for that cuff, to improve safety.

In the U.S. patent application Ser. No. 11/198,565, (hereafter the "Parent Application") of which the present application is a continuation-in-part, McEwen et al. describe apparatus for appropriately limiting the usage of a specific tourniquet cuff so that its usage does not exceed a safe usage limit for that cuff, to improve safety. For example, the apparatus of the Parent Application can limit the number of usages of a specific non-sterile, reusable tourniquet cuff so that usage of the cuff does not exceed a safe maximum number. Also, the apparatus of the Parent Application can limit the usage of reusable tourniquet cuffs manufactured as re-sterilizable to usage and re-sterilization within safe limits, including for example limiting the cumulative inflation time, the maximum inflation pressure, the number of cycles of usage and re-sterilization, or the overall duration of usage from time of manufacture due to ageing of cuff materials. Further, the Parent Application also describes apparatus that can limit the usage of a single-use tourniquet cuff to usage within safe usage limits, and to usage in only one surgical procedure, without relying on the detection of re-sterilization to indicate possible reuse, because some users may attempt to reuse single-use cuffs as non-sterile cuffs, without exposing them to re-sterilizing agents and re-sterilization processes between successive usages. The apparatus of the Parent Application also describes a tourniquet instrument connector containing a cuff usage register interface that is located within a predetermined distance from the tourniquet cuff containing a cuff usage register so that cuff usage records can be read from, and written into, the register.

DETAILED DESCRIPTION OF THE PREFERRED EMBODIMENT

Figure 1:
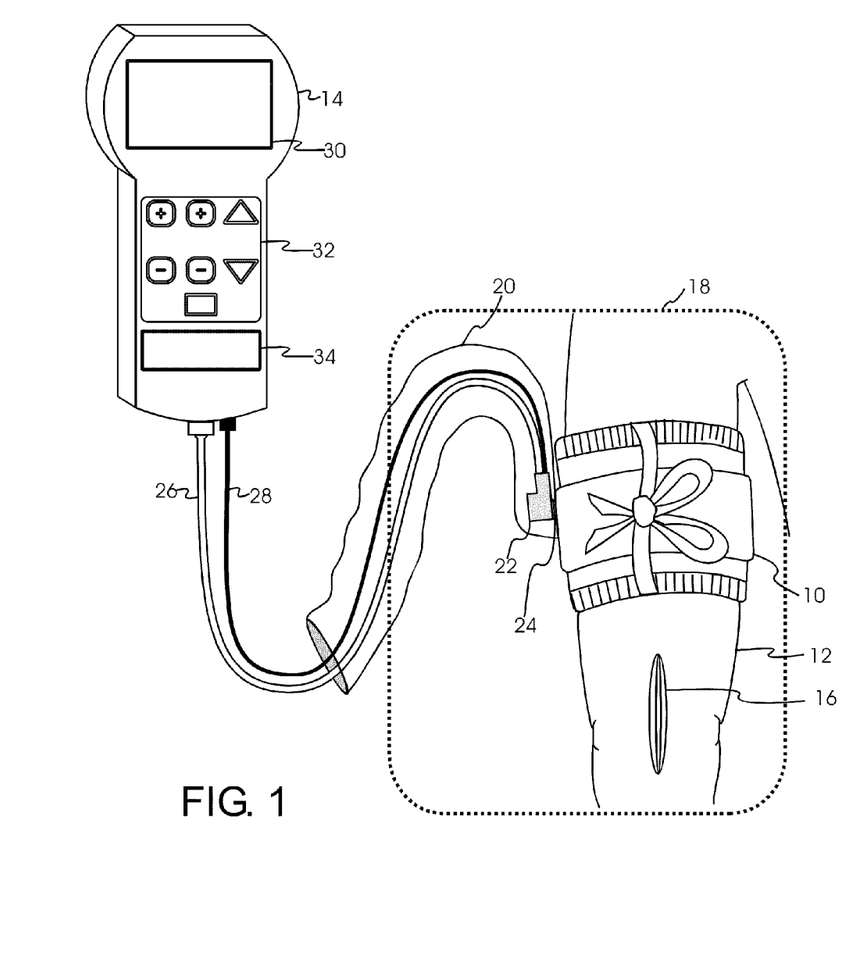
FIG. 1 is a pictorial representation of one preferred embodiment in a surgical application.

FIG. 1 is a pictorial representation of the preferred embodiment in a surgical application, showing tourniquet cuff 10 applied to patient limb 12 and pneumatically connected to tourniquet instrument 14. Patient limb 12 is shown with a surgical site 16. The perimeter of a sterile surgical field 18 encloses surgical site 16, a portion of patient limb 12, tourniquet cuff 10, and a portion of transparent flexible sheath 20. Creating and maintaining a sterile surgical field is an essential aspect of aseptic technique. To minimize the risk of infection of surgical site 16 only sterile objects and sterile portions of surgical staff may be allowed within the area of sterile field 18.

Within sheath 20, tourniquet instrument connector 22 mates with cuff connector 24 (shown in detail in FIGS. 3, 4, 5A, 5B, and 5C) on cuff 10 to form a releasable pneumatic connection to the inflatable portion of cuff 10. A pneumatic connection between instrument 14 and the inflatable portion of cuff 10 is formed when instrument connector 22 is mated with cuff connector 24, as shown in FIG. 1 and FIG. 5C. Instrument connector 22 is pneumatically connected to instrument 14 by flexible plastic tourniquet instrument tubing 26 and is electrically connected to instrument 14 by multi-conductor cable 28.

Instrument 14, tubing 26, cable 28, and instrument connector 22 are not sterile. The surfaces of instrument 14, tubing 26, cable 28, and connector 22 are typically wiped clean by the clinical user with an appropriate cleaning and disinfecting agent. This level of cleaning does not produce sterile surfaces and is typical of the cleaning and disinfecting of non-sterile equipment used in surgical operating rooms.

To permit cuff 10 to be used in sterile surgical field 18, cuff 10 may be sterilized at time of manufacture by exposure to a sterilizing agent within a sterilizing process determined to be safe and effective by the manufacturer, and may be supplied as a sterile product. Alternatively, it will be apparent that cuff 10 may be supplied as a non-sterile product by the manufacturer and may be sterilized subsequently by surgical staff, using a sterilizing process appropriate for cuff 10, prior to use in sterile field 18. For example, cuff 10 may be manufactured to withstand the temperatures and humidity associated with an autoclaving process for sterilization, and surgical staff may then autoclave cuff 10 prior to use in surgical field 18.

Figure 2:
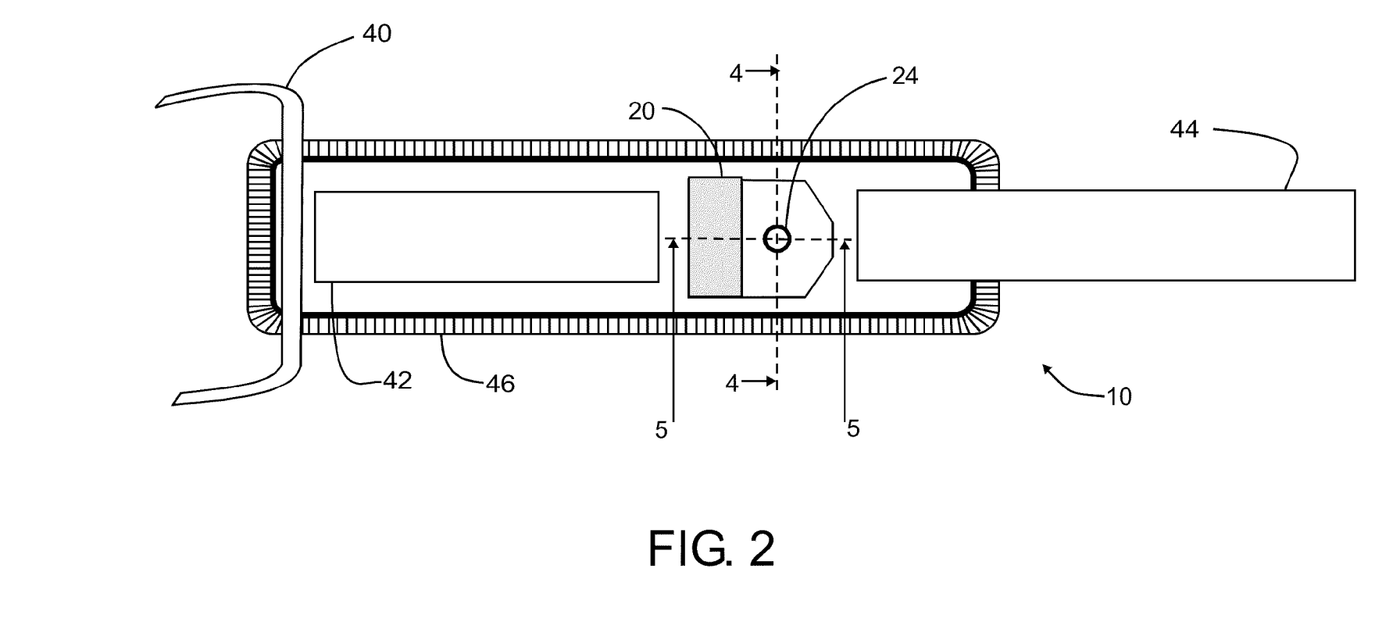
FIG. 2 is a top view of the cuff portion of the preferred embodiment.
Figure 3:
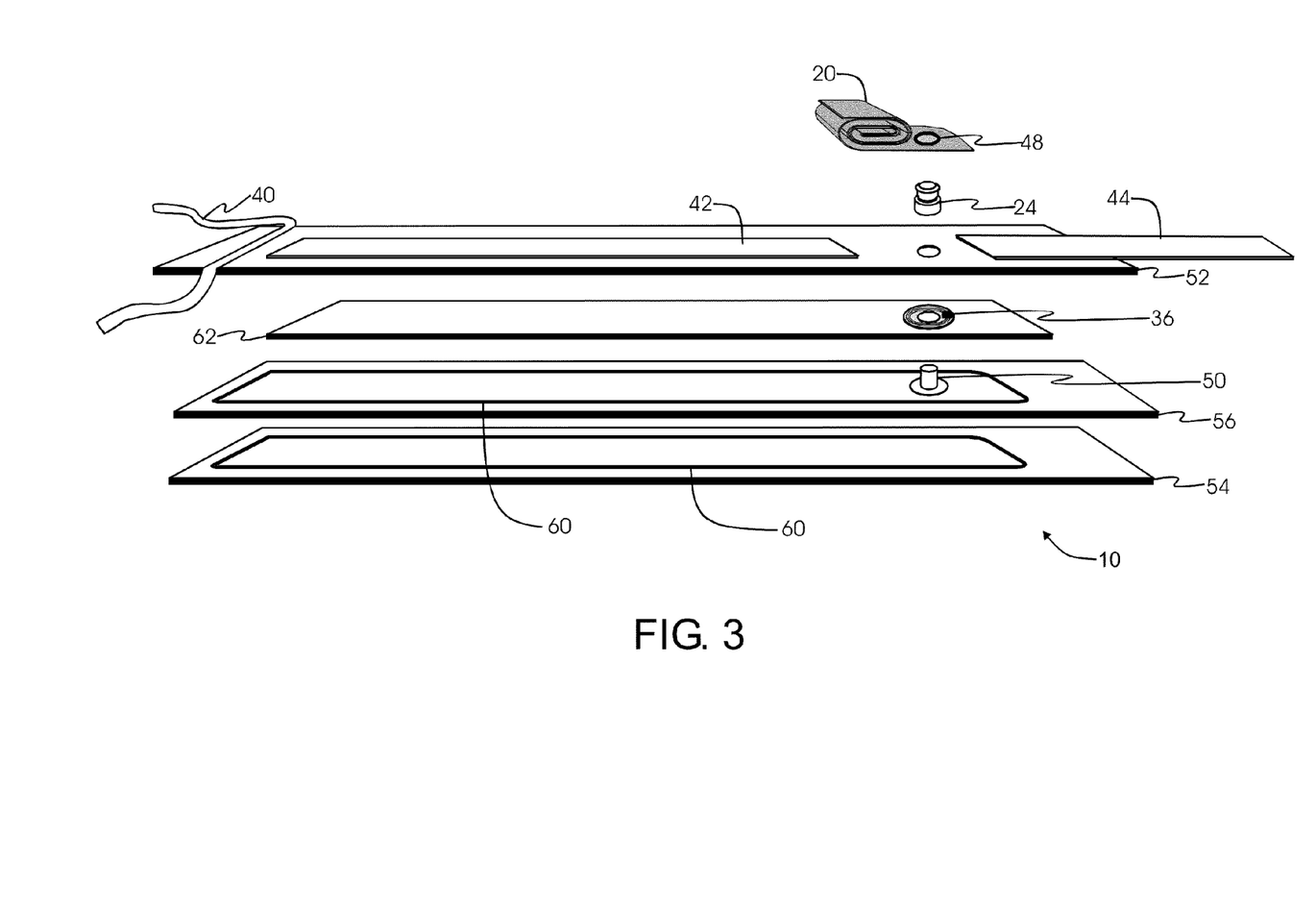
FIG. 3 is an exploded view of the cuff portion the preferred embodiment.
Figure 5A:
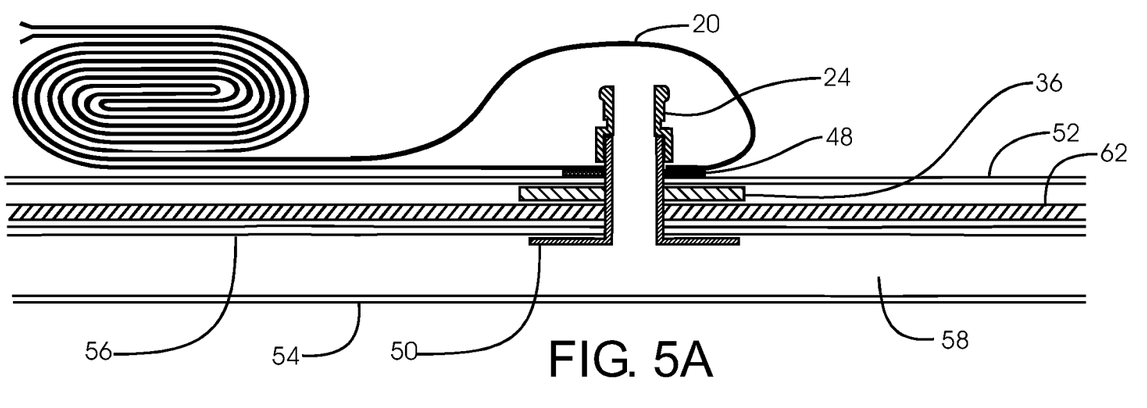
FIG. 5A is a partial section of the cuff taken from FIG. 2.

To permit a pneumatic connection to be made between the inflatable portion of cuff 10 and instrument 14 without compromising the integrity of sterile surgical field 18, cuff 10 includes transparent flexible sheath 20. Sheath 20 is permanently attached to cuff 10 and stored as a roll on cuff 10 near the location of cuff connector 24 as shown in FIGS. 2, 3, and 5A. It will be apparent that sheath 20 may adapted to releasably attach to cuff 10 at the location of cuff connector 20, allowing sheath 20 to be sterilized by a process that is different than the process used to sterilize cuff 10, thus allowing sterile sheath 20 to be attached to a cuff sterilized by another process. For example, sheath 20 may be sterilized by exposure to gamma radiation at time of manufacture and supplied as a sterile product for connection by surgical staff to a reusable cuff that has been adapted for sterilization by an autoclaving process in a hospital setting.

To connect instrument connector 22 to cuff connector 24 to form a pneumatic connection between cuff 10 and instrument 14, without compromising the integrity of sterile surgical field 18, sheath 20 is first extended beyond the perimeter of sterile surgical field 18 as shown in FIG. 1. Non-sterile instrument connector 22, tubing 26 and cable 28 are then passed through the conduit formed by sheath 20 to cuff connector 24. The size and shape of the thin flexible transparent material of sheath 20 allows a sterile user to manipulate instrument connector 22 through sheath 20 to connect it to cuff connector 24. The inner surface of sheath 20 is non-sterile as soon as contact is made with instrument connector 22, tubing 26 or cable 28, but the outer surface of sheath 20 that remains inside sterile field 18 continues to be sterile. Sheath 20 is constructed of material selected to form an impervious barrier to microorganisms that might otherwise contaminate sterile field 18 and infect surgical site 16.

Instrument 14 shown in FIG. 1 has a user interface consisting of pressure and time display panel 30, keypad 32 and cuff usage display panel 34. Pressure and time display panel 30 is employed for the selective display of any of the following alphanumeric information: actual cuff pressures as measured by instrument 14; reference or "set" cuff pressure levels, alarm reference "limits" or values; alphanumeric alarm messages describing detected alarm conditions and other information required for the operation of instrument 14.

Keypad 32 provides a means for a user of instrument 14 to control the operation of instrument 14. Keypad 32 includes an "inflate" key to initiate the inflation of cuff 10, a "deflate" key to initiate the deflation of cuff 10, and other keys to permit the user of instrument 14 to adjust the reference pressure level and set a time limit for an inflation time alarm.

When cuff 10 is pneumatically connected to tourniquet instrument 14, cuff usage display panel 34 is employed to indicate a record of the usage of cuff 10 and predetermined usage limits.

To improve patient safety by minimizing the risk of malfunction or failure of cuff 10 during a surgical procedure, the preferred embodiment maintains a record of cuff usage. The preferred embodiment may also inhibit further usage and alert a surgical user if cuff usage has exceeded a predetermined limit, as described below.

Integral to cuff 10 is a cuff usage register 36 shown in FIGS. 3, 4, 5A, 5B and 5C. Cuff usage register 36 is located inside cuff 10 at a predetermined distance from the end of cuff connector 24. As described further below, cuff usage register 36 is used to maintain a record of usage of cuff 10 and predetermined usage limits.

In the preferred embodiment cuff usage register 36 is comprised of a radio frequency transponder with memory (RA-117-112A, Texas Instruments, Dallas, Tex.). Physically, usage register 36 is 33 mm in diameter with an 18 mm diameter center hole and consists of a small integrated circuit bonded to a thin flexible polymer film substrate on which an aluminum foil antenna is patterned. The electronic circuits and antenna necessary for communication with usage register 36 are located within instrument connector 22 and comprise cuff usage register interface 38 which is shown in the cross sections in FIGS. 5B and 5C and in the block diagram in FIG. 6. Cuff usage register interface 38 within instrument connector 22 connects to instrument 14 via multi-conductor cable 28. The configuration of the electronic circuits and antenna comprising usage register interface 38 within instrument connector 22 limits communication with cuff usage register 36 to a distance of approximately 10 mm. This limited communication range, and the associated physical proximity and orientation of cuff usage register 36 to the end of cuff connector 24, helps assure that reliable and successful communication with cuff usage register 36 is limited to periods during which a gas-tight pneumatic connection to cuff connector 24 is established.

In the preferred embodiment, cuff usage register 36 contains a detailed record of the usage of cuff 10 as well as predetermined usage limits. The usage limits and usage record include:

An Inflation Cycle Limit, defined to be a predetermined limit of the number of inflation cycles which cuff 10 may safely undergo. In the preferred embodiment an inflation cycle is the pressurization of cuff 10 to a level above an Inflation Cycle Pressure Limit for a period of time greater than an Inflation Cycle Time Limit before deflation to a pressure less than the Inflation Cycle Pressure Limit;

An Inflation Cycle Pressure Limit, defined to be a predetermined pressure limit used to specify the inflation cycle described above;

An Inflation Cycle Time Limit, defined to be a predetermined time limit that is used to specify the inflation cycle described above;

A Maximum Pressure Limit, defined to be a predetermined value representing the maximum pressure to which cuff 10 may be safely pressurized;

An Inflation Time Limit, defined to be a predetermined value representing the total duration of time during which cuff 10 may be safely pressurized;

An End of Usage Date, defined to be a predetermined value representing the calendar date after which date cuff 10 may no longer be safely used;

The Number of Cycles of Inflation, a value corresponding to the number of inflation cycles that cuff 10 has undergone;

The Maximum Pressure of Inflation, a value representing the maximum pressure to which cuff 10 has been pressurized;

The Cumulative Time of Inflation, a value representing the total amount of time that the cuff has been pressurized above a predetermined minimum pressure.

Usage register 36 also contains a cuff identification record that uniquely identifies cuff 10 and indicates the physical characteristics of cuff 10.

When instrument 14 is pneumatically connected to cuff 10, instrument 14 reads information from cuff usage register 36 and displays this information on cuff usage display 34. As described further below, instrument 14 also updates the information in usage register 36 based on the pressurization of cuff 10 while connected to instrument 14 and inhibits further pressurization of cuff 10 if the usage limits contained within cuff usage register 36 are exceeded.

Cuff Materials and Construction

As described below, cuff 10 is constructed of materials that are appropriate for a single use disposable cuff manufactured for use inside a sterile surgical field for a single surgical procedure. Alternatively, it will be appreciated that cuff 10 may be constructed of materials that are appropriate for a reusable cuff, wherein the materials are selected to withstand multiple cleanings and sterilizations between surgical procedures by surgical staff using agents, methods and processes recommended by the manufacturer of cuff 10.

FIG. 2 is a top view of cuff 10 of the preferred embodiment laid flat. Cuff 10 is similar in design and construction to the cuffs described by McEwen in U.S. Pat. No. 5,741,295, U.S. Pat. No. 5,649,954, U.S. Pat. No. 5,484,831 and by Robinette-Lehman in U.S. Pat. No. 4,635,635. In the preferred embodiment shown, cuff 10 is rectangular with a length sufficient to encircle an adult arm as shown in FIG. 1. Those skilled in the art will appreciate that the sheath and usage register described in the preferred embodiment may also be incorporated in cuffs of various sizes and shapes, such as those described by McEwen in U.S. Pat. No. 5,649,954. It will also be appreciated that a usage register may be integral to sterilizable reusable tourniquet cuffs manufactured for usage within the sterile surgical field in multiple surgical procedures in conjunction with cleaning and sterilization by specified sterilization processes between successive procedures; and to disposable tourniquet cuffs manufactured as sterile products suitable for usage within the sterile surgical field in one surgical procedure and for disposal after the procedure.

In addition to usage register 36 described above, cuff 10 shown in FIG. 2 includes sheath 20, cuff connector 24, tie ribbon 40, loop material 42, hook material 44 and edge trim 46.

In use, cuff 10 is wrapped snugly around limb 12 (see FIG. 1) and secured circumferentially around the limb when the user engages hook material 44 to loop material 42. Tie ribbon 40 is a soft fabric ribbon material (Grosgrain ⅝" wide, Dynatex Textiles Inc., Toronto, Ontario, Canada) and allows the user to pull cuff 10 snug around the limb. When cuff 10 is in position and secured circumferentially around the limb, the user ties tie ribbon 40 as shown in FIG. 1 to help prevent the cuff from sliding proximally or distally on the limb when inflated. Edge trim 46 is made of similar material to tie ribbon 40 and helps prevent chafing of the patient's limb by the edges of cuff 10.

Prior-art sterile disposable cuffs intended for use in a sterile surgical field have long ports to permit connections to a tourniquet instrument to be made outside of the sterile field. These long ports have a number of disadvantages: they may interfere with the application of the cuff to the limb; they may inadvertently make contact outside of the sterile field during cuff application and may thus contaminate the cuff or surgical personnel; they add to the cost of cuff manufacture; they may increase pneumatic flow resistance affecting the accuracy of cuff pressure indication and regulation; and may increase the likelihood of partial or complete occlusions of the pneumatic passageway. Unlike prior-art cuffs with long ports, cuff 10 includes sheath 20 which encloses cuff connector 24 and is stored in a compact form as a roll on the top surface of cuff 10. Sheath 20 overcomes the disadvantages of cuffs with long ports: the compactly rolled sheath 20 that is stored on the surface of cuff 10 prior to unrolling does not interfere with the application of cuff 10 to patient limb 12; the cost of sheath 20 is less than the cost of extended length ports; and when unrolled sheath 20 permits a direct pneumatic connection to be made to sterile cuff 10 by enclosing non-sterile instrument connector 22, a portion of non-sterile instrument tubing 26 and a portion of non-sterile cable 28.

FIG. 3 is an exploded view of the layers and components that comprise cuff 10. In the preferred embodiment sheath 20 is a conduit formed from a 36-inch length of 2 mil thick transparent polyethylene film tubing. One end of the polyethylene film tubing is closed by a heat sealing process. A circular opening having a diameter substantially equivalent to the diameter of cuff connector 24 in the wall of the tubing near the closed end allows cuff connector 24 to protrude into the inside of sheath 20. A flexible double-sided adhesive ring 48 is used to retain sheath 20 to the top surface of cuff 10 around the opening for cuff connector 24 such that cuff connector 24 and a portion of cuff port 50 are enclosed within sheath 20, thereby forming an impervious barrier to micro-organisms. It will be apparent that sheath 20 may be adapted to releasably attach to cuff 10, by for example replacing adhesive ring 48 with a ring of elastic material bonded to sheath 20 to form a barrier around cuff connector 24 and to retain sheath 20 to cuff 10.

In FIG. 3 top layer 52 is shown with loop material 42, hook material 44 and tie ribbon 40 attached. Top layer 52 and bottom layer 54 are made of woven nylon cloth coated with thermoplastic material (for example, 200 Denier nylon cloth coated on one surface with thermoplastic polyurethane 0.006" thick) on the surface facing middle layer 56. Middle layer 56 is made of thermoplastic sheet material (for example, 0.020" thick polyurethane). In FIG. 3 cuff port 50 is shown bonded to middle layer 56. Cuff port 50 is molded from thermoplastic material and has a flange which is bonded to middle layer 56 to form pneumatic passageway extending into the inflatable portion of cuff 10, inflatable bladder 58, shown in FIGS. 4, 5A, 5B and 5C. The flange surface of cuff port 50 is permanently joined to middle layer 56 by a heat sealing process similar to that used to form bladder seal 60, described below. Cuff connector 24 is also molded from thermoplastic material, and the physical shape and outer surface of cuff connector 24 is adapted for connecting to instrument connector 22 to form a gas-tight pneumatic passageway at the connection. Cuff connector 24 is permanently bonded to cuff port 50. It will be appreciated that cuff port 50 and cuff connector 24 may be molded together to form a single component for attachment to middle layer 56.

Stiffener 62 is made of plastic sheet having greater stiffness than layers 52, 54, and 56 but flexible enough to be wrapped around the limb (for example 0.020 inch polyethylene sheet), and cut to a rectangular shape fitting within the perimeter of cuff 10.

Cuff usage register 36 is adhesively bonded to stiffener 62 concentric to the location where cuff port 50 passes through stiffener 62. This configuration insures correct orientation and location for reliable communication with usage register interface 38 when instrument connector 22 is mated with cuff connector 24.

Top layer 52, middle layer 56, and bottom layer 54 are joined around a continuous perimeter within the perimeter of cuff 10 at bladder seal 60, thereby forming inflatable bladder 58 (shown in FIGS. 4, 5A, 5B and 5C) between middle layer 56 and bottom layer 54 and enclosing thermoplastic stiffener 62 and cuff usage register 36 between top layer 52 and middle layer 56. When secured circumferentially around the limb as shown in FIG. 1, stiffener 62 helps direct the expansion of inflatable bladder 58 radially inwards towards the limb upon inflation of the cuff to more uniformly distribute pressure onto limb 12.

Bladder seal 60 is formed by a heat and pressure joining process, typically radio-frequency welding using a selected sealing die. The heat of the joining process is selected to temporarily melt a portion of the thermoplastic materials in layers 52, 54, and 56, causing them to fuse together in the area of bladder seal 60. A similar joining process is used to bond cuff port 50 to middle layer 56.

Figure 4:
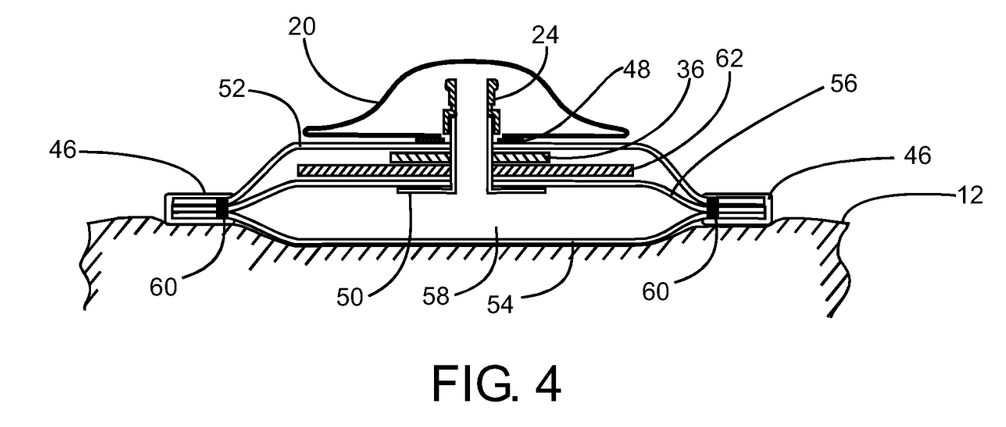
FIG. 4 is a section taken from FIG. 2, with the cuff applied to the patient's limb as shown in FIG. 1.

FIG. 4 is a cross section 4 taken from FIG. 2, with cuff 10 applied to limb 12 (as shown in FIG. 1) with cuff 10 shown inflated. As described above, inflatable bladder 58 is shown between middle layer 56 and bottom layer 54. The pneumatic passageway formed by cuff port 50 and cuff connector 24 is also clearly shown in FIG. 4.

Cuff usage register 36 is shown positioned on stiffener 62 such that cuff port 50 passes through cuff usage register 36 thereby ensuring cuff usage register 36 maintains its position in proximity to cuff connector 24.

Cuff 10 has an outer surface defined by the outer surfaces of top layer 52, bottom layer 54 and cuff connector 24. Cuff usage register 36 is enclosed within the outer surface of cuff 10 at predetermined position and orientation adapted to permit short range wireless communication with usage register interface 38 when cuff connector 22 is mated with cuff connector 24. Enclosing usage register 36 within the outer surface of cuff 10 provides protection for cuff usage register 36 from damage that may occur during the use and cleaning of cuff 10. Cuff usage register 36 cannot be removed from cuff 10 or tampered with, without causing obvious physical damage to the outer surface of cuff 10.

It will be apparent that other components could be selected to form cuff register 36 and that cuff register 36 could be enclosed within the outer surface of cuff 10 by being embedded within cuff connector 24 such that cuff register 36 retains the correct orientation and distance from the end of cuff connector 24 to permit communication with usage register interface 38 when instrument connector 22 is mated with cuff connector 24 to establish a gas-tight pneumatic passageway at the connection. It will also be apparent that the length of cuff port 50 may be increased and an appropriately adapted cuff connector 24 attached so as to permit communication with cuff usage register 36.

FIG. 5A is a partial longitudinal cross-section 5 of cuff 10 shown in FIG. 2. As shown in FIG. 5A sheath 20 encloses cuff connector 24 and is illustrated rolled up and stored on the top surface of cuff 10.

Figure 5B:
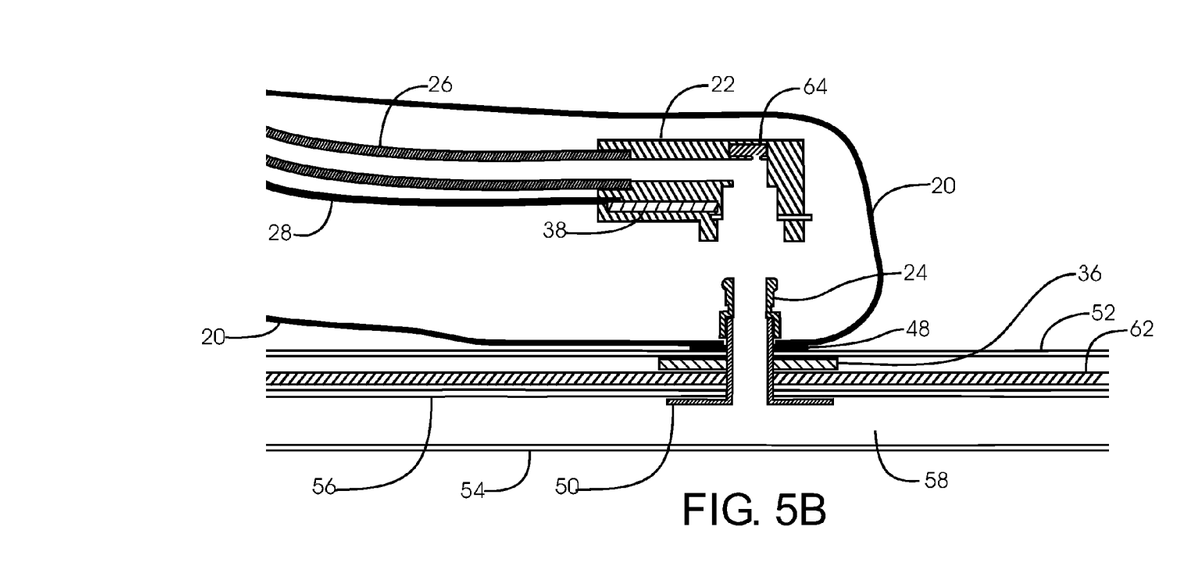
FIG. 5B is a partial section of the cuff taken from FIG. 2 also showing a section of the instrument connector.
Figure 5C:
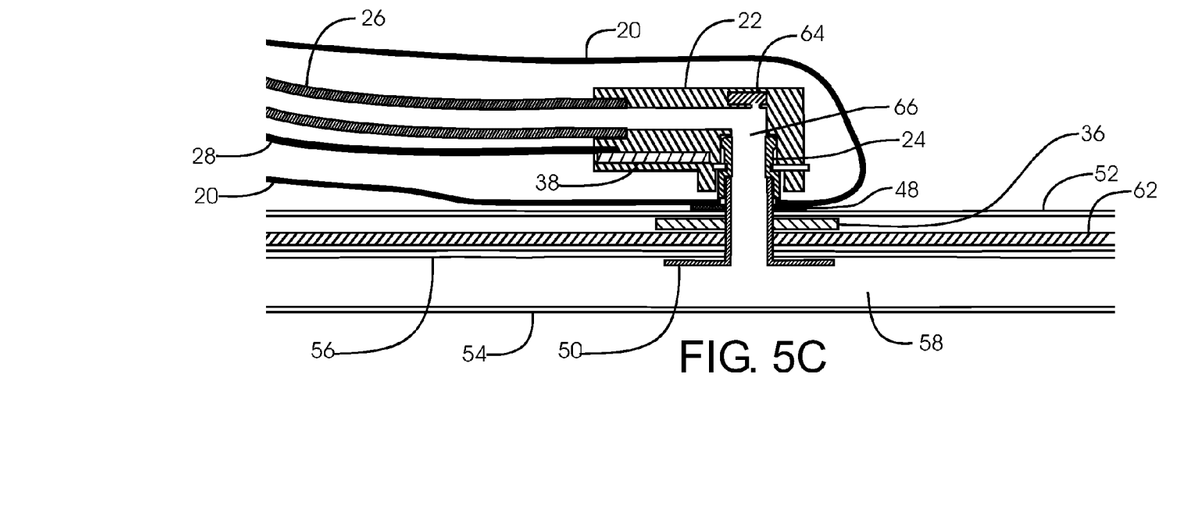
FIG. 5C is a partial section of the cuff taken from FIG. 2 also showing a section of the instrument connector mated with the cuff connector.

To enable a better understanding of the preferred embodiment and the pneumatic connection between instrument 14 and the inflatable portion of cuff 10, FIGS. 5B and 5C have been provided. FIGS. 5B and 5C are partial cross-sections (5) of cuff 10 in FIG. 2. FIGS. 5B and 5C are illustrated with sheath 20 deployed and containing instrument connector 22 and a portion of instrument tubing 26 and cable 28. Instrument connector 22, tubing 26 and cable 28 are shown in cross-section in FIGS. 5B and 5C.

Referring first to FIG. 5B instrument connector 22 is shown ready to mate with cuff connector 24. The cross section of instrument connector 24 depicts usage register interface 38, the pneumatic passageway with instrument connector 22 and cuff pressure transducer 64. Cuff pressure transducer 64 communicates pneumatically with the pneumatic passageway within instrument connector 22 and thereby directly with inflatable bladder 58 when cuff connector 24 is connected to instrument connector 22 to form a gas-tight pneumatic passageway at the connection. Cuff pressure transducer 64 generates a cuff pressure signal representative of the pressure within cuff 10 which is communicated to instrument 14 via multi-conductor cable 28.

FIG. 5C shows instrument connector 22 mated with cuff connector 24 within sheath 20. The pneumatic passageway 66 formed at the connection between instrument connector 22 and cuff connector 24 directly couples pressure transducer 64 to inflatable bladder 58, thus enabling pressure transducer 64 to directly and accurately indicate the pressure of gas within inflatable bladder 58. As described below an accurate and direct indication of the pressure of gas within cuff 10 is critical to the proper control of the pressure of gas within cuff 10 by instrument 14.

Instrument Hardware

Figure 6:
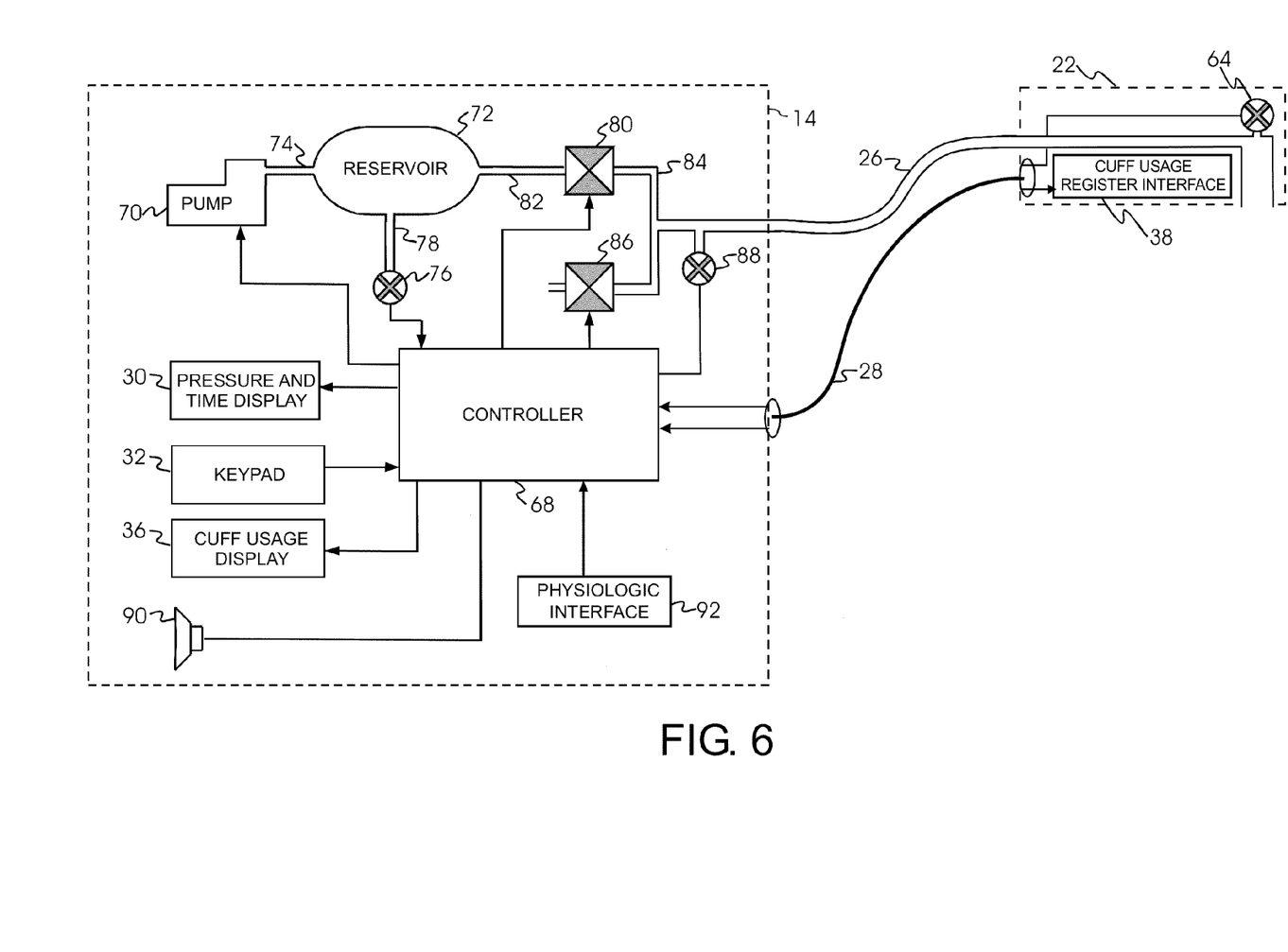
FIG. 6 is a block diagram of the preferred embodiment.

Referring to the block diagram of instrument 14 shown in FIG. 6, controller 68 comprises a microcontroller (AT-MEGA128, Atmel Corp., San Jose, Calif.), associated memory and control software, analog and digital peripheral interface circuitry, timers, real time clock and other necessary support components.

As shown in FIG. 6, pneumatic pump 70 is pneumatically connected to reservoir 72 by tubing 74. In response to control signals from controller 68, pump 70 operates to pressurize reservoir 72. Reservoir pressure transducer 76 is pneumatically connected by tubing 78 to reservoir 72 and generates a reservoir pressure signal. The reservoir pressure signal is communicated to controller 68. Controller 68 acts to maintain the pressure in reservoir 72 near a reservoir pressure level, typically 100 mmHg greater than the cuff reference pressure level. Controller 68 in response to the reservoir pressure level and the reservoir pressure signal activates pump 70 to maintain the level of the reservoir pressure signal near the reservoir pressure level.

Inflation valve 80 (EVO-3-12V, Clippard Instrument Laboratory, Cincinnati, Ohio) is configured as a two position normally closed valve. One side of the valve is pneumatically connected via tubing 82 to reservoir 72 the other side of the valve is connected to inflatable bladder 58 within cuff 10 via the pneumatic passageway formed by manifold 84, tubing 26, instrument connector 22, cuff connector 24 and cuff port 50. When energized by controller 68, inflation valve 80 moves to the open position and allows pressurized gas to flow from reservoir 72 to cuff 10, thereby increasing the pressure of gas in the inflatable bladder 58 of cuff 10.

Deflation valve 86 (EVO-3-12V, Clippard Instrument Laboratory, Cincinnati, Ohio) is configured as a two position normally closed valve. One side of the valve is pneumatically connected to cuff 10 via the pneumatic passageway formed by manifold 84, tubing 26, instrument connector 22, cuff connector 24 and cuff port 50, the other side is open to atmosphere. When energized by controller 68, deflation valve 86 moves to the open position and allows pressurized gas to flow from cuff 10 to atmosphere, thereby decreasing the pressure of gas in inflatable bladder 58 within cuff 10.

Manifold pressure transducer 88 is pneumatically connected to manifold 84 and generates a manifold pressure signal representative of the pressure within manifold 84 which is communicated to controller 68.

As shown in FIG. 6 cuff pressure transducer 64 is located within instrument connector 22 as described above and communicates pneumatically with the gas passageway within instrument connector 22 and thereby directly with inflatable bladder 58 when cuff connector 24 is connected to instrument connector 22 to form a gas-tight pneumatic passageway at the connection. Cuff pressure transducer 64 generates a cuff pressure signal representative of the pressure within cuff 10 which is communicated to controller 68 via multi-conductor cable 28.

The direct pneumatic connection between inflatable bladder 58 of cuff 10 and cuff pressure transducer 64 provides for an accurate indication of the actual pressure of gas within cuff 10 at any time. Pressure transducer 64 will continue to accurately indicate the pressure of gas within cuff 10 even if tubing 20 should become occluded during use.

It will be apparent that transducer 64 could be located within cuff 10 to be in direct communication with inflatable bladder 58 and coupled to controller 68 via the same or similar wireless interface employed between usage register interface 38 and cuff usage register 36.

As noted above, controller 68 will, in response to generated alarm signals alert the user of an alarm condition by the display of appropriate alarm messages on pressure and time display 30 and by producing audible tones. Speaker 90 is connected to controller 68, and electrical signals having different frequencies to specify different alarm signals and conditions are produced by controller 68 and converted to audible sound by loud speaker 90.

Physiologic interface 92 provides a means for controller 68 to interface with and receive information from physiologic sensors. Controller 68 may if desired, automatically adjust the cuff pressure reference level in response information received from physiologic sensors via physiologic sensor interface 92. For example, the cuff pressure reference level may be automatically adjusted by controller 68 in response to a sensor for determining the minimum effective cuff pressure within cuff 10 required for occluding blood flow past cuff 10. Also, controller 68 may automatically adjust the cuff pressure reference level in response to changes in venous pressure which may occur during intravenous regional anesthesia, and in response to changes in other physiologic parameters such as blood pressure.

Pressure Regulation

A user of instrument 14 may use keypad 32 to select a reference pressure level; this is the pressure of gas that instrument 14 will attempt to maintain in the inflatable portion of cuff 10 when cuff 10 is inflated. Controller 68 will generate high or low pressure alarm signals if the pressure in cuff 10 cannot be maintained near the selected reference pressure level. If the cuff pressure level exceeds the reference pressure level by 15 mmHg a high pressure alarm signal will be generated by controller 68. If the cuff pressure level falls below the reference pressure level by 15 mmHg a low pressure alarm signal will be generated by controller 68.

When instrument connector 22 is mated with cuff connector 24 and controller 68 detects that the "inflate" key on keypad 32 has been depressed by a user of instrument 14, controller 68 first tests, as described further below, to ensure the usage limit for cuff 10 has not been exceeded. If the cuff usage limit has been exceeded the user is alerted by messages displayed on display panels 30 and 34 and by audio tones, and controller 68 does not proceed to inflate cuff 10. If the usage limit for cuff 10 has not been exceeded, controller 68 operates to inflate cuff 10 to a pressure near the selected reference pressure level and to then regulate the pressure in cuff 10 near the reference pressure level until such time that controller 68 detects that the "deflate" key on keypad 32 has been depressed by a user of instrument 14. Controller 68 may also inflate, adjust the reference pressure level, and deflate cuff 10 automatically in response to signals from physiologic interface 92.

To inflate and regulate the pressure in cuff 10 controller 68 includes a pressure regulator; the pressure regulator in the preferred embodiment is implemented as a control algorithm that operates as described below. At regular predetermined regulation intervals of 40 ms controller 68 computes a pressure error signal. The pressure error signal corresponds to the difference between the reference pressure level and the cuff pressure level. Controller 68 uses the pressure error signal as a term in a proportional integral control algorithm to calculate activation time intervals for inflation valve 80 and deflation valve 86. To increase the gas pressure in cuff 10 when the cuff pressure signal is below the reference pressure level, the activation time interval for deflation valve 86 is set to zero and the activation time interval for inflation valve 80 is proportional to the magnitude of the pressure error signal and the integral of the pressure error signal. To decrease the gas pressure in cuff 10 when the cuff pressure signal is above the reference pressure level, the activation time interval for inflation valve 80 is set to zero and the activation time interval for deflation valve 86 is proportional to the magnitude of the pressure error signal and the integral of the pressure error signal. Controller 68 limits the maximum valve activation time intervals of valve 80 and valve 86 to the regulation interval time (40 ms). It will be appreciated by those skilled in the art that alternate pressure regulation algorithms could be employed to control the activation of inflation valve 80 and deflation valve 86 in response to a cuff pressure signal and a reference pressure level, or that proportional valves could be used instead of the valves used in the preferred embodiment.

In order to correctly regulate the pressure of gas in cuff 10 at a pressure near the cuff pressure reverence level and correctly indicate over and under pressure alarm conditions, controller 68 must have available an accurate indication of the pressure within the inflatable portion of cuff 10. In the preferred embodiment the accurate measurement of the pressure of gas in cuff 10 is facilitated by cuff pressure transducer 64 and the direct pneumatic connection between the inflatable portion of cuff 10 and transducer 64. Unlike prior art tourniquets which depend upon a flexible pneumatic channel which may become occluded between the inflatable portion of the cuff and a pressure transducer located within the body of an instrument, the connection between the inflatable portion of cuff 10 and transducer 64 is made within the rigid pneumatic passageway of instrument connector 22 and cannot be occluded by external manipulation of instrument connector 22.

While regulating the pressure within cuff 10, controller 68 compares the level of the manifold pressure signal with the level of the cuff pressure signal. If the level of the manifold pressure level differs substantially from the cuff pressure signal controller 68 acts to alert the user that an occlusion of tubing 26 or other fault condition may have occurred.

Cuff Usage Register

Referring again to the block diagram in FIG. 6, controller 68 communicates with cuff usage display 34 to display information obtained from cuff usage register 36 which is integral to cuff 10.

To read and write information to cuff usage register 36 controller 68 sends commands and data to cuff usage register interface 38 located in instrument connector 22. Usage register interface 38 communicates with controller 68 via multiconductor cable 28. Usage register interface 38 responds to commands from controller 68 to detect the presence of usage register 36, to read values from usage register 36, and to write values to usage register 36.

Controller 68 polls usage register interface 38 to detect the presence of usage register 36. When instrument connector 22 is mated with cuff connector 24 to establish a gas-tight pneumatic passageway at the connection, thus allowing usage register interface 38 to establish communication with cuff usage register 36, usage register interface 38 communicates to controller 68 that usage register 36 has been detected and values may now be read from and written to usage register 36. When instrument connector 22 is not connected to cuff connector 24 and the presence of usage register 36 is not detected by controller 68, controller 68 acts to inhibit activation of the pressure regulator described above and to display a message on cuff usage display 34 to indicate that a pneumatic connection has not been established to cuff 10.

Cuff usage register 36 contains non-volatile electrically alterable memory. Values representing amounts and limits of cuff usage may be both written to and read from selected memory locations within cuff usage register 36. Selected memory locations may also be configured as read only which inhibits the further writing and updating of values in these locations. Memory locations may be written to and then configured as read only at the time cuff 10 is manufactured.

Memory locations containing values representing usage limits are written with predetermined values at the time cuff 10 is manufactured and then configured as read only locations to prevent any subsequent modification of the limits. Usage limits are chosen at the time of manufacture to ensure continued safe operation of cuff 10 within the confines of the construction methods and physical materials used in the manufacture of cuff 10.

Memory locations containing values representing a record of cuff usage are configured as read/write so that they may be updated by controller 68 via usage register interface 38 when cuff 10 is pressurized.

As defined above, in the preferred embodiment the usage limits stored in usage register 36 are as follows: Inflation Cycle Limit; Inflation Cycle Pressure Limit; Inflation Cycle Time Limit; Maximum Pressure Limit; Inflation Time Limit; and End of Usage Date. Also, as defined above the usage record stored in usage register 36 includes the following: Number of Cycles of Inflation; Maximum Pressure of Inflation; and Cumulative Time of Inflation.

Other memory locations are used to store values to uniquely identify cuff 10 and to represent information regarding the physical characteristics of cuff 10 such as: cuff length, the cuff type, the cuff shape, and recommended cuff pressures. For example, instrument 14 may be configured with two independent pressure regulators, associated pneumatics and usage register interfaces to permit it to independently pressurize two cuff bladders such as is required for a dual-bladder tourniquet cuff used for Bier block anesthesia. Cuff and bladder identification information stored in the usage register for each cuff bladder can be used by instrument 14 to alert the operator that the cuff is correctly identified, that the two sets of tubing and connectors from the tourniquet instrument are correctly connected to the matching proximal and distal bladders, and that the tourniquet pressure setting is appropriate for the identity and characteristics of the connected dual-bladder cuff.

In the preferred embodiment usage limits are established and set at the time of cuff manufacture and usage records are modified only by tourniquet instrument 14. It will be apparent that various security methods known in the art could be used to prevent unauthorized modification of the contents of usage register 36 by instruments other than tourniquet instrument 14.

When instrument connector 22 is mated with cuff connector 24 and controller 68 confirms that usage register 36 has been detected and that values may be read from and written to usage register 36, controller 68 reads and stores in its internal memory the usage limits and usage record from usage register 36, via usage register interface 38. Controller 68 then displays these values on cuff usage display 36.

Controller 68 next compares the usage record to the usage limits as follows: The Number of Cycles of Inflation is compared with the Inflation Cycle Limit, if the Number of Cycles of Inflation is equal to or greater than the Inflation Cycle Limit a warning message is displayed on cuff usage display 34 and the inflation of cuff 10 is inhibited; the Maximum Pressure of Inflation is compared with the Maximum Pressure Limit, if the Maximum Pressure of Inflation is greater than the Maximum Pressure Limit a warning message is displayed and the inflation of cuff 10 is inhibited; the Cumulative Time of Inflation is compared with the Inflation Time Limit, if the Cumulative Time of Inflation is greater than the Inflation Time Limit a warning message is displayed and the inflation of cuff 10 is inhibited; the End of Usage Date is compared with the current date and if the current date is greater than the End of Usage Date a warning message is displayed on cuff usage display 34 and the inflation of cuff 10 is inhibited.

In addition, controller 68 acts to limit the maximum cuff reference pressure selectable by a user of instrument 14 to the Maximum Pressure Limit for cuff 10 retrieved from cuff usage register 36. This prevents an operator from selecting pressure levels that are potentially damaging to cuff 10.

If controller 68 does not detect that any usage limit for cuff 10 has been exceeded, controller 68 proceeds, as described above, to pressurize cuff 10 when a user of instrument 14 activates the "inflate" key on keypad 32.

In the preferred embodiment, controller 68 inhibits inflation of cuff 10 if the usage limit has been exceeded. It will be apparent that controller 68 could be configured to allow inflation of cuff 10 when a usage limit has been exceeded by requiring the operator to use keypad 32 to acknowledge that the usage limit for cuff 10 has been exceeded before inflating cuff 10.

To update the Number of Cycles of Inflation controller 68 operates as follows. Controller 68 monitors the cuff pressure level as indicated by cuff pressure transducer 64. When the cuff pressure level exceeds the Inflation Cycle Pressure Limit retrieved from cuff usage register 36, controller 68 starts a timer, this timer continues to run while the cuff pressure level remains above the Inflation Cycle Pressure Limit and measures the duration of time that the pressure level exceeds the limit. When the cuff pressure level does not exceed the Inflation Cycle Pressure Limit, controller 68 stops and resets this timer. When the time indicated by the timer exceeds the Inflation Cycle Time Limit, controller 68 increments the Number of Cycles of Inflation by 1 and writes via usage register interface 38 the updated value to usage register 36.

In the preferred embodiment the Inflation Cycle Pressure Limit and the Inflation Cycle Time Limit are used to define what level and duration of pressurization of cuff 10 is considered to be an Inflation Cycle. These limits can be selected so as to permit the functional testing of cuff 10 using appropriate test methods by operating-room staff between successive usages, and the testing by biomedical engineering staff on a periodic basis, without such testing affecting the available Number of Cycles of Inflation of the cuff.

To update the Maximum Pressure of Inflation controller 68 monitors the cuff pressure level as indicated by cuff pressure transducer 64. If at any time the cuff pressure level exceeds the Maximum Pressure of Inflation, controller 68 sets the Maximum Pressure of Inflation to the cuff pressure level and writes via usage register interface 38 the updated value to usage register 36. This ensures that the usage record for cuff 10 reflects the peak pressure to which cuff 10 has been exposed. Controller 68 also compares the cuff pressure level to the Maximum Pressure Limit and alerts the operator by displaying an alarm message and activating an audio tone if the cuff pressure level exceeds the Maximum Pressure Limit.

In the preferred embodiment the Cumulative Time of Inflation is measured in minutes. To update the Cumulative Time of Inflation controller 68 increments the Cumulative Time of Inflation and writes the updated value to usage register 36 each minute that the cuff pressure level remains above a predetermined minimum pressure level. In the preferred embodiment the predetermined minimum pressure level is the same as the Inflation Cycle Pressure Limit used to determine usage cycles. It will be apparent that alternate pressure limits could be used and the limit predetermined by controller 68 or recorded as a separate limit in cuff usage register 36.

Examples of Typical Use

To enable a better understanding of the preferred embodiment and the function of the cuff usage record and limits, examples of the preferred embodiment's typical use in surgical procedures are described below.

In this first example cuff 10 is a single use disposable tourniquet cuff which is sterilized by the manufacturer and supplied in a sterile state to the user. Cuff 10 includes sheath 20 which is permanently attached. Due to the materials and methods used in the manufacture of this cuff the usage limits stored in cuff usage register 36 are predetermined by the manufacturer to be: Inflation Cycle Limit 1; Inflation Cycle Pressure Limit 50 mmHg; Inflation Cycle Time Limit 10 minutes; Maximum Pressure Limit 400 mmHg; Inflation Time Limit 240 minutes. Cuff 10 is selected for application to a patient for use during a surgical procedure, the area surrounding the operative site is cleaned and disinfected by surgical personnel and a sterile surgical field established. Cuff 10 is applied to the patient's limb by personnel working within the sterile field. To connect cuff 10 to instrument 14, sheath 20 is extended beyond the perimeter of the sterile surgical field, instrument connector 22, tubing 26 and cable 28 are fed into sheath 20 by personnel working outside of the sterile field. Personnel working within the sterile surgical field manipulate instrument connector 22 through sheath 20 to connect it to cuff connector 24. Instrument 14 then reads and displays the usage limits above and the usage record of cuff 10. The usage record from cuff 10 shows the following usage: Number of Cycles of Inflation 0; Maximum Pressure of Inflation 0 mmHg, Cumulative Time of Inflation 0 minutes. Because cuff 10 has not been previously used the usage record shows 0 values.

The operator selects a cuff reference pressure of 250 mmHg. Because none of the usage limits have been exceeded, instrument 14 will permit cuff 10 to be pressurized when the user activates the "inflate" key on keypad 32. Cuff 10 is inflated for a total of 80 minutes during the surgical procedure. At the end of the surgical procedure cuff usage register 36 contains the following record of cuff usage: Number of Cycles of Inflation 1; Maximum Pressure of Inflation 250 mmHg, Cumulative Time of Inflation 80 minutes. In this example the Number of Cycles of Inflation now equals the Inflation Limit stored in usage register 36 in cuff 10. If cuff 10 is subsequently connected to instrument 14, instrument 14 will detect that the usage limit for this cuff has been exceeded and alert the operator and inhibit pressurization of cuff 10. This prevents cuff 10 from being used beyond the usage limits set by the manufacturer for the safe and effective use of cuff 10.

Another example of the typical use of the preferred embodiment in surgical procedures is as follows. In this example, cuff 10 is constructed of materials that are chosen to withstand sterilization by steam autoclave and cuff 10 is autoclaved before being applied to the patient. The manufacturer has performed testing and determined usage limits for the cuff that will permit cuff 10 to be used safely and re-sterilized under normal conditions. The usage limits stored in cuff usage register 36 are: Inflation Cycle Limit 10; Inflation Cycle Pressure Limit 50 mmHg; Inflation Cycle Time Limit 10 minutes; Maximum Pressure Limit 500 mmHg; Inflation Time Limit 1200 minutes.

Cuff 10 is selected for application to a patient for use during a surgical procedure, the area surrounding the operative site is cleaned and disinfected by surgical personnel and a sterile surgical field established. Cuff 10 is applied to the patient's limb by personnel working within the sterile field. Sheath 20 is sterilized by the manufacturer and supplied in a sterile state to the user separate from cuff 10. To connect cuff 10 to instrument 14, sheath 20 is applied to cuff 10 such that it encloses cuff connector 24, it is then extended beyond the perimeter of the sterile surgical field, instrument connector 22, tubing 26 and cable 28 are fed into sheath 20 by personnel working outside of the sterile field. Personnel working within the sterile surgical field manipulate instrument connector 22 through sheath 20 to connect it to cuff connector 24. Instrument 14 then reads and displays the usage limits above and the usage record of cuff 10. The usage record from cuff 10 shows the following usage: Number of Cycles of Inflation 7; Maximum Pressure of Inflation 300 mmHg, Cumulative Time of Inflation 600 minutes. Because none of the usage limits have been exceeded, instrument 14 will permit cuff 10 to be pressurized when the user activates the "inflate" key on keypad 32. The operator next selects a cuff reference pressure of 300 mmHg. Cuff 10 is inflated for a total of 60 minutes during the surgical procedure. At the end of the surgical procedure cuff usage register 36 contains the following record of cuff usage:

Number of Cycles of Inflation 8; Maximum Pressure of Inflation 300 mmHg, Cumulative Time of Inflation 660 minutes. Note that the Number of Cycles of Inflation has increased by 1 and Cumulative Time of Inflation has increased by 60 minutes. In this example, cuff 10 has 2 remaining inflation cycles that it can be subjected to in subsequent surgical procedures before instrument 14 inhibits further pressurization of cuff 10.

The embodiment illustrated is not intended to be exhaustive or limit the invention to the precise form disclosed. It is chosen and described in order to explain the principles of the invention and its application and practical use, and thereby enable others skilled in the art to utilize the invention. For example, it will be appreciated by those skilled in the art that the cuff usage register may be adapted to include apparatus for directly measuring usage of the cuff during surgery, to include apparatus for writing the measured usage into the cuff usage register, and to include any power source required for such measuring and writing, so that the adapted cuff usage register may operate without interaction with the tourniquet instrument and while completely contained within the cuff. It will be also be appreciated by those skilled in the art that the cuff usage register may be adapted so that the cuff usage record contained within the cuff usage register may be read by apparatus other than a tourniquet instrument, or may be read by a tourniquet instrument when the pneumatic passageway to the cuff is not established, to allow the prior usage of the cuff to be determined for quality assurance purposes and for other useful purposes.

We claim:

1. A tourniquet cuff apparatus comprising:
   a cuff having an inflatable portion and a length sufficient to encircle a limb of a patient;
   the cuff including a port communicating pneumatically with the inflatable portion of the cuff, the port having a cuff connector;
   a tourniquet instrument connector mating with the cuff connector to define a connection passageway between the two connectors that communicates pneumatically with the inflatable portion of the cuff;
   a connection transducer mounted external to a remote tourniquet instrument and adjacent to the connection passageway and configured to sense the pressure in the connection passageway and to generate and wirelessly transmit a connection pressure signal representing the pressure within the inflatable portion of the cuff, wherein the connection transducer is mounted to the tourniquet instrument connector and movable therewith into and out of mating connection with the cuff connector;
   an interface for receiving the wirelessly transmitted connection pressure signal, wherein the interface is mounted to the tourniquet instrument connector;
   a continuous flexible tube extending from the tourniquet instrument connector to the tourniquet instrument to define therebetween a tube pneumatic passageway communicating pneumatically with the connection passageway;
   an internal transducer mounted internal to the tourniquet instrument and arranged for detecting the pressure in the tube pneumatic passageway and providing a second pressure signal representing the pressure in the connection passageway;
   a signal conducting member for conveying the connection pressure signal received by the interface to the remote tourniquet instrument, the signal conducting member is located outside of the flexible tube and has one end connected to the interface and an opposing end connected to the instrument; and
   a controller connected to the tourniquet instrument for receiving and comparing the connection pressure signal and the second pressure signal and for initiating a fault alert in instances when those two signals vary by more than a predetermined minimum.

2. The apparatus of claim 1 wherein the cuff connector is carried on the cuff, and further comprising a shroud mounted on the cuff in a retracted position to enclose the cuff connector and to be extendable therefrom to enable the mating of the cuff connector and tourniquet instrument connector inside the shroud and enclosing a portion of the signal conducting member.

3. The apparatus of claim 1 wherein the signal conducting member is a signal-carrying wire extending from the connection transducer to the tourniquet instrument.

4. The apparatus of claim 3 wherein the connection transducer is located between the tube and the cuff and adjacent to the connection passageway and wherein the signal carrying wire and tube are enclosable within a shroud that is mounted to the cuff and to be extendable therefrom.

5. The apparatus of claim 1 wherein the connection transducer is a pressure transducer having a portion thereof exposed to the connection passageway.

6. The apparatus of claim 1 wherein the cuff connector is arranged so that the connection passageway is adjacent to the cuff.

7. The apparatus of claim 1 further comprising:
   a register attached to the cuff and having recorded thereon information relating to the cuff; and
   the interface and configured to read from the register the information relating to the cuff when the interface and register are within a predetermined, limited communication range.

8. The apparatus of claim 7 wherein the interface is connected for transmitting the read information to the remote tourniquet instrument.

9. The apparatus of claim 7 wherein the interface is mounted to the cuff connector and configured to write to the register information relating to the cuff when the interface and register are within a predetermined, limited communication range.

10. A tourniquet cuff apparatus comprising:
    a cuff having an inflatable portion and a length sufficient to encircle a limb of a patient;
    the cuff including a port communicating pneumatically with the inflatable portion of the cuff, the port having a cuff connector;
    a tourniquet instrument connector mating with the cuff connector to define a connection passageway between the two connectors that communicates pneumatically with the inflatable portion of the cuff;
    a connection transducer mounted external to a remote tourniquet instrument and adjacent to the connection passageway and configured to sense the pressure in the connection passageway and to generate a connection pressure signal representing the pressure within the inflatable portion of the cuff;
    a flexible tube extending from the tourniquet instrument connector to the tourniquet instrument to define therebetween a continuous pneumatic passageway communicating pneumatically with the connection passageway;
    an internal transducer mounted internal to the tourniquet instrument and arranged for detecting the pressure in the continuous pneumatic passageway and wirelessly transmitting a second pressure signal representing the pressure in the continuous pneumatic passageway;

an interface mounted to the tourniquet instrument connector and configured for receiving the wirelessly transmitted second pressure signal;

a signal conducting member having one end connected to the interface and extending outside of the flexible tube and outside of the pneumatic passageway to the tourniquet instrument; and a controller connected to the tourniquet instrument and to a second end of the signal conducting member for receiving and comparing the connection pressure signal and the second pressure signal and for initiating a fault alert in instances when those two signals vary by more than a predetermined minimum.

11. The apparatus of claim 10 further comprising:

a register attached to the cuff and having recorded thereon information relating to the cuff; and the interface being configured to read from the register the information relating to the cuff when the interface and register are within a predetermined, limited communication range.

12. A method of operating a tourniquet cuff having an inflatable portion and a length sufficient to encircle a limb of a patient and a port communicating pneumatically with the inflatable portion of the cuff, comprising the steps of:

providing the port with a cuff connector;

mating the cuff connector with a tourniquet instrument connector to define a connection passageway between the two connectors that communicates pneumatically with the inflatable portion of the cuff;

sensing the pressure in the connection passageway with a connection transducer mounted external to a remote tourniquet instrument and adjacent to the connection passageway, and generating a connection pressure signal representing the pressure within the inflatable portion of the cuff;

wirelessly transmitting the connection pressure signal from the connection transducer to an interface that is mounted to the tourniquet instrument connector;

providing a flexible tube extending from the tourniquet instrument connector to the tourniquet instrument for defining therebetween a continuous pneumatic passageway communicating pneumatically with the connection passageway;

conducting the connection pressure signal from the interface along a signal conducting member that is external to the flexible tube;

mounting an internal transducer to the tourniquet instrument and detecting the pressure in the continuous pneumatic passageway, and providing a second pressure signal representing the pressure in the continuous pneumatic passageway; and receiving and comparing the connection pressure signal and the second pressure signal and initiating a fault alert in instances when those two signals vary by more than a predetermined minimum.

13. The method of claim 12 further comprising the steps of:

attaching to the cuff a register and recording thereon information relating to the cuff; and configuring the interface to read from the register the information relating to the cuff when the interface and register are within a predetermined, limited communication range.

\* \* \* \* \*